United States Patent
Schneider

(10) Patent No.: US 12,414,957 B2
(45) Date of Patent: Sep. 16, 2025

(54) CANNABIDIOL COMPOSITIONS FOR THE TREATMENT OF INFLAMMATION

(71) Applicant: RevRx, LLC, Houston, TX (US)

(72) Inventor: Aaron Michael Schneider, Houston, TX (US)

(73) Assignee: RevRx, LLC, Houston, TX (US)

( * ) Notice: Subject to any disclaimer, the term of this patent is extended or adjusted under 35 U.S.C. 154(b) by 56 days.

(21) Appl. No.: 18/334,565

(22) Filed: Jun. 14, 2023

(65) Prior Publication Data

US 2023/0338303 A1 Oct. 26, 2023

Related U.S. Application Data

(63) Continuation of application No. 16/932,164, filed on Jul. 17, 2020, now Pat. No. 11,717,493.

(60) Provisional application No. 62/876,143, filed on Jul. 19, 2019.

(51) Int. Cl.
| | | |
|---|---|---|
| *A61K 36/00* | (2006.01) | |
| *A61K 31/045* | (2006.01) | |
| *A61K 31/05* | (2006.01) | |
| *A61K 31/125* | (2006.01) | |
| *A61K 36/28* | (2006.01) | |
| *A61K 36/324* | (2006.01) | |
| *A61K 47/10* | (2017.01) | |
| *A61P 29/00* | (2006.01) | |

(52) U.S. Cl.
CPC ............ *A61K 31/05* (2013.01); *A61K 31/045* (2013.01); *A61K 31/125* (2013.01); *A61K 36/28* (2013.01); *A61K 36/324* (2013.01); *A61K 47/10* (2013.01); *A61P 29/00* (2018.01)

(58) Field of Classification Search
None
See application file for complete search history.

(56) References Cited

U.S. PATENT DOCUMENTS

| | | |
|---|---|---|
| 9,375,417 B2 | 6/2016 | Smith et al. |
| 2011/0104301 A1 | 5/2011 | Ahern |
| 2018/0284402 A1 | 10/2018 | Hoag |
| 2021/0015763 A1 | 1/2021 | Schneider |

OTHER PUBLICATIONS

Raskin et al. (2004) Current Pharmaceutical Design 10: 3419-3429. (Year: 2004).*
Revilla et al. (1998) J. Agric. Food Chem. 46: 4592-4597 (Year: 1998).*
Sharma et al. (2010) Inter. J. Phytomedicine 2: 94-99. (Year: 2010).*
Tallarida (2011) Genes & Cancer 2(11): 1003-1008. (Year: 2011).*
Baron, Eric P. "Medicinal Properties of Cannabinoids, Terpenes, and Flavonoids in Cannabis, and Benefits in Migraine, Headache, and Pain: An Update on Current Evidence and Cannabis Science" Headached, Jul./Aug. 2018, 1139-1186.
Guimaraes, et al. "Terpenes and derivatives as a new perspective for pain treatment: a patent review" published online Jan. 6, 2014, Expert Opinion on Therapeutic Patents, 24:3, 243-265.
Human Science, LLC, Human Science Pain Relief Cream, label and ingredients, Revised Aug. 2019.
Iannitti, et al. "Effectiveness and Safety of Arnica montana in Post-Surgical Setting, Pain and Inflammation" American Journal of Therapeutics 23, e184-e197 (2016).
Janero, et al. "Terpenes and Lipids of the Endocannabinoid and Transien••Receptor-Potential-Channel Biosignaling Systems" dx.doi. org/10.1021/cn5000875 I,ACS Chem. Neurosci. 2014, 5, 1097-1106.
Medterra Pain Relief Cream, label and list of ingredients.
Naternal, Rescue CBD Muscle Cream, information about product from website and list of ingredients.
Sager Pharma KFT., Salanpas Powerful Pain Relief Patch, information about product from website. 2022.
Scifinder, Research Topic—menthol and cannabinoids, Jan. 24, 2022, 3 pp.
Genuine Virgin Aloe Corp., Triderma Pain Relief Cream, drug facts and active ingredients, product label, revised Oct. 2019, 4 pp.
Yue, et al. "Study on Terpenoid Compounds of Different Tissues of Camphor Tree" Advances in Biological Sciences Research (ABSR), vol. 4, 171-177.

* cited by examiner

*Primary Examiner* — Russell G Fiebig
(74) *Attorney, Agent, or Firm* — Edwin S. Flores; Daniel J. Chalker; Chalker Flores, LLP

(57) ABSTRACT

The present invention includes composition and methods for treating inflammation and/or pain, the composition comprising: hemp cannabidiol (cannabinoid) 0.1%-0.6% weight percent; menthol 3.0-4.0% weight percent; *Arnica montana* 0.1-5.0% weight percent; camphor 0.1-5.0% weight percent; *Bosweila serrata* extract 0.1-5.0% weight percent; camphor terpene 0.1-5.0% weight percent; isopropyl alcohol <30% weight percent; glycerin <6.0% weight percent; and qs with water.

7 Claims, No Drawings

CANNABIDIOL COMPOSITIONS FOR THE TREATMENT OF INFLAMMATION

CROSS-REFERENCE TO RELATED APPLICATIONS

This application is a continuation application of U.S. application Ser. No. 16/932,164 filed Jul. 17, 2020 entitled "CANNABIDIOL COMPOSITIONS FOR THE TREATMENT OF INFLAMMATION" which claims priority to U.S. Provisional Application Ser. No. 62/876,143, filed Jul. 19, 2019, the entire contents of each are incorporated herein by reference.

TECHNICAL FIELD OF THE INVENTION

The present invention relates in general to the field of compositions and methods for treating inflammation, and more particularly, to compositions that include hemp oil cannabidiol to treat inflammation and pain related thereto.

STATEMENT OF FEDERALLY FUNDED RESEARCH

Not applicable.

BACKGROUND OF THE INVENTION

Without limiting the scope of the invention, its background is described in connection with treatments for pain.

Presently, the over-use of oral over-the-counter Non-steroidal anti-inflammatory drugs (NSAIDs), and the lack of available topical over-the-counter pain relief alternatives has led to the need for new methods and composition for treating inflammation and pain.

One such patent is U.S. Pat. No. 9,375,417, which relates to transdermal cannabinoid formulations that include tetrahydrocannabinol (THC), as an active component to the formulation's effectiveness. The formulations taught also include anti-convulsants, anti-psychotics, anti-oxidants, neuroprotective agents, anti-cancer agents, and have immunomodulatory effects.

U.S. Patent Publication US 2018/0284402A1 identifies several formulations that contain Hemp Oil Cannabidiol with less than 0.3% TCH. Briefly, these applicants teach using cannabinoid compounds in hydrophilic compositions comprised of synthetic and natural plant extract compounds that are multifunctional TRPM8 ion channel agonists, TRPA1 and TRPV1 ion channel antagonists, CGRP antagonists, COX-2 inhibitors and CB1 and CB2 antagonists. These applicants further teach a topical analgesic composition comprising at least one synthetic or natural plant extract TRPM8 agonist, at least one synthetic or natural plant extract that is a TRPA1 antagonist, and fixed plant seed oil containing Omega-3 fatty acids TRPV1 antagonists and a carrier.

What is needed are natural topical and analgesic pain relief and methods to reduce neuropathic inflammatory pain.

SUMMARY OF THE INVENTION

In one embodiment, the present invention includes a composition comprising: hemp cannabidiol (cannabinoid); menthol; camphor; herb extract; and qs with water. In one aspect, the composition further comprises at least one of isopropyl alcohol, or propylene glycol. In another aspect, the composition further comprises at least delivery vehicle or gel selected from: glycerin, Carbomer (polyacrylic acid), Hydrated Silica, Aminomethyl Propanol, or Methyl Paraben. In another aspect, the herb extract is selected from at least one of *Arnica montana* Extract, Camphor Terpene Extract, *Bosweila serrata* Extract, *Uricaria tomentosa* Extract, or *ILEX paraguariensis* Leaf Extract. In another aspect, the composition further comprises one or more inactive ingredients selected from at least one of: Isopropyl Alcohol, Propylene Glycol, Glycerin, Carbomer 940, Hydrated Silica, Aminomethyl Propanol or Methyl Paraben. In another aspect, the amount of menthol is 0.1-0.6 weight percent. In another aspect, the amount of menthol is less than 0.5 weight percent. In another aspect, the amount of menthol is about 3.0 to 5.0 weight percent. In another aspect, the composition is defined further as comprising hemp cannabidiol (cannabinoid) 0.1-0.6 weight percent; menthol 3.0-4.0 weight percent; *Arnica montana* 0.1-5.0 weight percent; camphor 0.1-5.0 weight percent; *Bosweila serrata* extract 0.1-5.0 weight percent; camphor terpene 0.1-5.0 weight percent; isopropyl alcohol <30 weight percent; glycerin <6.0 weight percent; and qs with water. In another aspect, the composition is free of any tetrahydrocannabinol.

In another embodiment, the present invention includes a composition consisting essentially of: hemp cannabidiol (cannabinoid) 0.1-0.6 weight percent; menthol 3.0-4.0 weight percent; *Arnica montana* 0.1-5.0 weight percent; camphor 0.1-5.0 weight percent; *Bosweila serrata* extract 0.1-5.0 weight percent; camphor terpene 0.1-5.0 weight percent; isopropyl alcohol <30 weight percent; glycerin <6.0 weight percent; and qs with water. In another aspect, the hemp cannabidiol is 0.16-0.17 weight percent. In another aspect, the composition is free of any tetrahydrocannabinol. In another aspect, the composition consists of: hemp cannabidiol (cannabinoid) 0.1-0.6 weight percent; menthol 3.0-4.0 weight percent; *Arnica montana* 0.1-5.0 weight percent; camphor 0.1-5.0 weight percent; *Bosweila serrata* extract 0.1-5.0 weight percent; camphor terpene 0.1-5.0 weight percent; isopropyl alcohol <30 weight percent; glycerin <6.0 weight percent; and qs with water.

In another embodiment, the present invention includes a method of treating inflammation, pain, or both comprising: providing an amount of a composition effective to reduce or eliminate inflammation, pain, or both, wherein the composition comprises: hemp cannabidiol (cannabinoid); menthol; *Arnica montana*; camphor; a herb extract; camphor terpene; glycerin; and qs with water to treat inflammation, pain, or both. In one aspect, the composition further comprises at least one of isopropyl alcohol, or propylene glycol. In another aspect, the composition further comprises at least delivery vehicle or gel selected from: glycerin, Carbomer (polyacrylic acid), Hydrated Silica, Aminomethyl Propanol, or Methyl Paraben. In another aspect, the herb extract is selected from at least one of *Arnica montana* Extract, Camphor Terpene Extract, *Bosweila serrata* Extract, *Uricaria tomentosa* Extract, or *ILEX paraguariensis* Leaf Extract. In another aspect, the composition further comprises one or more inactive ingredients selected from at least one of: Isopropyl Alcohol, Propylene Glycol, Glycerin, Carbomer 940, Hydrated Silica, Aminomethyl Propanol or Methyl Paraben. In another aspect, the amount of menthol is 0.1-0.6 weight percent. In another aspect, the amount of menthol is less than 0.5 weight percent. In another aspect, the amount of menthol is about 3.0 to 5.0 weight percent. In another aspect, the composition is defined further as comprising hemp cannabidiol (cannabinoid) 0.1-0.6 weight percent; menthol 3.0-4.0 weight percent; *Arnica montana* 0.1-5.0 weight percent; camphor 0.1-5.0 weight percent;

*Bosweila serrata* extract 0.1-5.0 weight percent; camphor terpene 0.1-5.0 weight percent; isopropyl alcohol <30 weight percent; glycerin <6.0 weight percent; and qs with water. In another aspect, the composition is free of any tetrahydrocannabinol.

BRIEF DESCRIPTION OF THE DRAWINGS

Not applicable.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

In another embodiment, the present invention includes a composition comprising two main active components, (1) Hemp Cannabidiol (0-THC) 500 mg (Tested 99% purity) (0.1-0.6%); and (2) Menthol 3.0-4.0% (3.5%). The composition may also include herbal extracts, including: (1) *Arnica montana*; (2) Camphor Terpene; (3) *Bosweila serrata* Extract; (4) *Uricaria tomentosa* Extract; and/or (5) *ILEX paraguariensis* Leaf Extract. Further, the composition can include one or more inactive components, such as: Water, Isopropyl Alcohol; Propylene Glycol; Glycerin; Carbomer 940; Hydrated Silica; Aminomethyl Propanol; and/or Methyl Paraben.

In another embodiment, the present invention includes a composition comprising: at least two active ingredients, and two alcohols: isopropyl alcohol, propylene glycol, agents comprising the delivery vehicle or gel: Glycerin, Carbomer (polyacrylic acid), Hydrated Silica, Aminomethyl Propanol, and Methyl Paraben. The active ingredients are: (1) Hemp Cannabidiol (0-THC) 500 mg (Tested 99% purity) (0.1-0.6%); and (2) Menthol 3.0-4.0% (3.5%). The composition can also include certain herbal extracts (5.0%) that have been found to synergize with the two active agents. These herbal extracts can include one or more of the following: (1) *Arnica montana*; (2) Camphor Terpene; (3) *Bosweila serrata* Extract; (4) *Uricaria tomentosa* Extract; and/or (5) *ILEX paraguariensis* Leaf Extract. In certain embodiments, the composition includes 1, 2, 3, 4, or all 5 herbal extracts. The composition can also include one or more of the following inactive Ingredients: Water, Isopropyl Alcohol; Propylene Glycol; Glycerin; Carbomer 940; Hydrated Silica; Aminomethyl Propanol; and/or Methyl Paraben.

The present invention shows the synergistic effects of Hemp Cannabidiol combined with Menthol to provide clinically significant reductions in musculoskeletal pain as compared to Hemp (0-THC) Cannabidiol, and Menthol alone. Current studies have revealed over 300 patients experiencing mild to severe pain benefited from the combination of Hemp cannabidiol in menthol.

Cannabidiol is a hydrophobic compound that is absorbed better through the skin than it is absorbed through the gut. Topical application avoids first pass liver metabolism, and irritation to the gut and GI lining. The formulation of the present invention was designed to be fast acting, long acting, dry quickly, and provide relief within seconds. The inactive base formulation is designed to assist in absorption, drying quickly with minimal residue, and scent.

The quick drying nature of the formulation allows it to be applied 10 minutes prior to exercise to provider relief prior to perspiration. The fast-acting nature of Menthol 3.5% in isopropyl alcohol provides immediate relief. The inactive base formulation provides long acting effects of menthol 3.5% localize to the skin with propylene glycol, carbomer, methyl paraben, hydrated silica, and glycerin.

The inactive base formulation adheres the formula to the skin such that the formulation stays in the applied area so that treatment and absorption of Cannabidiol and Menthol can be absorbed into the target area.

Case Studies.

Case #1: A 76 year old Caucasian male with a history of rheumatoid arthritis (RA), and debilitating joint pain. Had recent orthopedic spinal fusion of C3-C4 vertebrae to provide stability and subsequent mobility. The patient started on a regimen of OxyContin® 5 mg 3-5 times a day as needed for pain for 3 days. The patient began with reporting a pain score of 10 immediately post-op while taking prescription pain management medication. After day 3, the patient began using Cryogel topically applied to the site of the pain 3-4 times a day. Cryogel tested was Hemp Cannabidiol (0-THC) 500 mg (Tested 99% purity) (0.1-0.6%), Menthol 3.0-4.0% (3.5%), Herbal Extracts (5.0%)(*Arnica montana*, Camphor Terpene, *Bosweila serrata* Extract, *Uricaria tomentosa* Extract, and *ILEX paraguariensis* Leaf Extract), inactive ingredients, and qs with water. Post-op pain begins to subside, and the patient was able to discontinue opioid pain management, while continuing to use only Cryogel topically. The patient 2 weeks post-op with 9 days of only topical Cryogel for 3-4 times daily is presenting with a pain score of 2-3 with 1 being no-pain, and 10 being the most pain he's ever experienced.

Patient is currently reporting a pain score of 1-3. Patient reporting: "Questioned if I would ever reach this level following my last surgery." "I still have discomfort, but mostly getting out of bed first thing in the morning, and rising up from a soft low sofa." "Your CBD product has been tremendous."

Case #2: A 66 year old Caucasian male with a history of injury, and exercise induced joint/muscle pain. Patient is very active, and an avid runner. Patient begins experiencing chronic knee pain, and muscle soreness in late November 2018, and had tried the following with minimal relief: Ibuprofen 200 mg: 4 TID with mild pain relief. Naproxen 375 mg ER: 2 TID with mild pain relief BIOFREEZE®: Applied topically to knee, and sore muscle. Patient began using Cryogel by applying the roll-on applicator to the knees, and or sore muscles post exercise. The patient has discontinued oral NSAIDs, and BIOFREEZE®, and has continued to use Cryogel as the sole source pain relief applicator.

Patient has continued to use Cryogel, and has seen significant pain, and soreness reduction to joints, and muscles. Patient reports applying Cryogel to joints and sore muscles as needed, and experience relief within minutes. Patient also reports pain relief to last 4-6 hours.

Case #3: A 56 year old Female with a history of and exercise induced joint/muscle pain. Patient is very active, and an avid runner. Patient begins experiencing chronic knee pain, and muscle soreness in late January 2019, and had tried the following with minimal relief: BIOFREEZE®: Applied topically to knee, and sore muscles 3-4 times day. Patient began using Cryogel by applying the roll-on applicator to the knees, and or sore muscles post exercise. The patient has discontinued BIOFREEZE®, and has continued to use Cryogel as the sole source pain relief applicator. After 4 days, patient continued to use Cryogel, and has seen significant pain, and soreness reduction to joints, and muscles.

Patient reports applying Cryogel to joints and sore muscles as needed, and experience relief within minutes. Patient also reports pain relief to last 4-6 hours.

Case #4: A 57 year old Male with a history of and exercise induced joint/muscle pain. Patient is very active: running, weightlifting, cycling, yoga. Patient begins experiencing chronic knee pain, and muscle soreness in late January 2019, and had tried the following with minimal relief: Ibuprofen 200 mg: 2 Tablets as needed. BIOFREEZE®: Applied topically to knee, and sore muscles 3-4 times day. Patient began using Cryogel by applying the roll-on applicator to the knees, and or sore muscles post exercise. The patient has discontinued BIOFREEZE®, and has continued to use Cryogel as the sole source pain relief applicator.

Follow-up at three weeks. Patient has continued to use Cryogel, and has seen significant pain, and soreness reduction to joints, and muscles. Patient reports applying Cryogel to joints and sore muscles as needed, and experience relief within minutes. Patient also reports pain relief to last at least 4 hours.

Case #5: A 33 year old male presenting complaint sore/stiff neck lasting 7 days. Patient is very active: running, weightlifting, cycling, yoga, swimming. Patient began experiencing neck and muscle soreness, after an upper extremity and shoulder workout on. Neck and muscle soreness prohibited any physical activity. Patient began taking the following three days later with limited relief. ALEVE® OTC Gel Caps: Take 2 Gel Capsules 3-4 times daily. Patient also had deep muscle tissue massage that provided minimal relief. Patient began using Cryogel five days after the injury, and began experiencing immediate relief. Patient reports pain, stiffness, and soreness resolved after 2 days of applying Cryogel 3-4 times daily. Follow-up two weeks later, patient reports no pain/soreness in neck, and is able to workout without fear or further injury.

Case #6: A 29 year old female presenting complaint of sore back, and ribs, after yoga workout. Patient is very active: running, weight-lifting, cycling, yoga, barre, kick-boxing. Patient begins experiencing back, and intercostal muscle soreness, shortly after a power yoga class Apr. 4, 2019. Patient began taking the following in an attempt to subside pain: ALEVE® OTC Gel Caps: Take 2 Gel Capsules 4 times daily. Patient began using Cryogel four days after the start of pain, and began experiencing immediate relief. Patient reports in upper back, and ribs resolved after 3 days of applying Cryogel 3-4 times daily. Follow-up 10 days later, patient reports no pain/soreness in back, and ribs and is able to resume intensive workouts without fear or further injury.

Case #7: A 46 year old male presenting with chronic lower back pain. Patient has history of RA, and has tried taking the following: Ibuprofen 500 mg—Take 1 Tablet QID. Naproxen 375 ER—Take 1 Tablet QID. Hydrocodone/APAP 5 mg/500 mg—Take 1-2 Tablets 3-4 Times daily. BIOFREEZE®—Apply topically to affected area as needed. Tramadol 50 mg—Take 1 Tablet TID. Tizanidine 4 mg—Take 1 Tablet BID. Patient has experienced limit pain relief. Patient presented to PCP requesting a Hydrocodone/APAP 5 mg/500 mg refill. PCP provider initiated Cryogel topically in office. Patient reported relief within a few minutes. Patient did not receive a refill for Hydrocodone/APAP 5 mg/500 mg. Patient purchased Cryogel, and has begun, a regimen of Cryogel, with Ibuprofen PRN. Follow-up approximately one month later, patient reports a significant reduction in pain score after initiating Cryogel. Patient will occasionally take an over the counter NSAID if additional relief needed.

Case #8: A 66 year old male diabetic presenting with peripheral neuropathy. Patient experiences burning, stinging pain in feet associated with peripheral neuropathy. Patient also has history of arthritis, and has tried taking the following: Ibuprofen 500 mg—Take 1 Tablet QID. LYRICA® 100 mg—Take 2-3 capsules as needed BID. Patient has experienced limit pain relief. PCP provider initiated Cryogel topically in office. Patient reported relief within a few minutes. Patient purchased Cryogel, and has begun, a regimen of Cryogel, with Ibuprofen PRN. Patient applies Cryogel to feet 2-3 Times daily for peripheral neuropathic pain in feet. Patient reports a significant reduction in stinging, burning, and discomfort after initiating Cryogel. Patient will occasionally take an over the counter NSAID if additional relief needed for RA.

Case #9: A 56 year old female presenting with quad pain associated with exercise. Patient experiences burning, and soreness in right quad. Patient reported trying the following to relieve soreness and pain: Soft Tissue Massage—provided limited relief Topical CBD Oil (local shop hand crafted)—No relief. cbdMD-brand Topical Roll on—no relief. CBD Oral Tincture 100 mg—no relief. Ibuprofen 200 mg—Take 2 tablets TID—no relief. Patient began applying Cryogel to quad area of muscle injury or tear, and begins experiencing relief within a few hours. Patient reports resolution of pain, and soreness after initiating Cryogel. Patient continues to use Cryogel as needed.

Case #10: Cryogel CBD 500 mg is a topical hemp applicator designed to assist in relieving joint, muscle, and arthritic aches and pains. 37 y/o male presenting with diagnosed, "Tennis Elbow," of the right elbow. Patient experiences burning, and soreness in right elbow, and shooting pain down the right arm. Patient reported trying the following to relieve soreness and pain: Soft Tissue Massage—Providing Limited Relief CBDMD Topical Roll on—No relief. Ibuprofen 200 mg—Take 2 tablets TID—No relief. Patient began applying Cryogel to right elbow of injury or tear, and begin experiencing relief within a few hours. 5 days later. Patient reports resolution of pain, and soreness after initiating Cryogel. Patient continues to use Cryogel as needed.

Case #11: Cryogel CBD 500 mg is a topical hemp applicator designed to assist in relieving joint, muscle, and arthritic aches and pains. 34 y/o male presenting with upper left trapezius muscle pain. Patient experiences burning, tightness, soreness to left shoulder, and upper back. Patient reported trying the following to relieve soreness and pain: Soft Tissue Massage—Providing Limited Relief. Menthol 10% —(BENGAY®)—No relief Ibuprofen 200 mg—Take 2 tablets TID—No relief Patient began applying Cryogel to trapezius muscle of injury or tear, and begin experiencing relief within a few hours. 2 days later. Patient reports resolution of pain, and soreness after initiating Cryogel. Patient continues to use Cryogel as needed.

Case #12: Cryogel CBD 500 mg is a topical hemp applicator designed to assist in relieving joint, muscle, and arthritic aches and pains. 30 y/o female presenting with neck and shoulder muscle pain. Patient experiences burning, tightness, soreness to left shoulder, and upper back. Patient reported trying the following to relieve soreness and pain: Soft Tissue Massage—Providing Limited Relief Menthol 10% —(BENGAY®)—No relief CBDMD 750 mg CBD Roll on—No relief. Patient began applying Cryogel to muscle of injury or tear, and begin experiencing relief within a few hours. 1 day later. Patient reports resolution of pain, and soreness after initiating Cryogel. Patient continues to use Cryogel as needed.

Case #13: Cryogel CBD 500 mg is a topical hemp applicator designed to assist in relieving joint, muscle, and arthritic aches and pains. 30 y/o male presenting with quadricep tear or strain and right leg muscle pain. Patient experiences burning, tightness, soreness to right quadricep. Patient reported trying the following to relieve soreness and pain: Naproxen 220 mg—Take 2 tablets TID—limited relief. Menthol 10% —(BENGAY®)—No relief. Patient began applying Cryogel to muscle of injury or tear, and begin experiencing relief within a few hours. 3 days later. Patient reports resolution of pain, and soreness after initiating Cryogel. Patient continues to use Cryogel as needed.

Case #14: Cryogel CBD 500 mg is a topical hemp applicator designed to assist in relieving joint, muscle, and arthritic aches and pains. 30 y/o female presenting with right calf muscle pain. Patient experiences burning, tightness, soreness to right quadricep. Patient reported trying the following to relieve soreness and pain: Ibuprofen 200 mg—Take 2 tablets TID—limited relief. Menthol 10% —(BENGAY®)—No relief. Patient began applying Cryogel to muscle of injury or tear, and began experiencing relief within a few hours. One month later. Patient reports resolution of pain, and soreness after initiating Cryogel. Patient continues to use Cryogel as needed.

Case #15: Cryogel CBD 500 mg is a topical hemp applicator designed to assist in relieving joint, muscle, and arthritic aches and pains. 30 y/o male presenting with ankle swelling, and soreness. Patient experiences swelling, soreness, tenderness to touch. Patient reported trying the following to relieve soreness and pain: Ibuprofen 200 mg—Take 2 tablets TID—limited relief. Menthol 10% —(BENGAY®)—No relief. Patient began applying Cryogel to muscle of injury or tear, and began experiencing relief within a few hours. One month later. Patient reports resolution of pain, and soreness after initiating Cryogel. Patient continues to use Cryogel as needed.

Case #16: Cryogel CBD 500 mg is a topical hemp applicator designed to assist in relieving joint, muscle, and arthritic aches and pains. 67 y/o female presenting with labrum tear post-surgical repair, pain and soreness. Patient experiences swelling, soreness, tenderness to touch, lack of mobility. Patient reported trying the following to relieve soreness and pain: Percocet—Take 1 tablet 4-6 hours for severe pain—moderate relief Ibuprofen 200 mg—Take 2 tablets BID—limited relief. Menthol 10% —(BENGAY®)—No relief. Patient began applying Cryogel to affected shoulder post-surgery, and began experiencing relief within a few hours. Patient began using Cryogel day 3 post-op surgery and discontinued Percocet and Ibuprofen after day 3. Patient continued to use Cryogel 500 mg topical roll on as mono-therapy in conjunction with physical therapy with sufficient pain relief. One week later. Patient reports resolution of pain, and soreness after initiating Cryogel. Patient continues to use Cryogel as needed.

Case #17: Cryogel CBD 500 mg is a topical hemp applicator designed to assist in relieving joint, muscle, and arthritic aches and pains. 63 y/o female presenting with sciatica nerve pain beginning in upper right hip area. Patient experiences burning, soreness, stinging pain, and sleeplessness. Patient reported trying the following to relieve soreness and pain: Ibuprofen 200 mg—Take 2 tablets TID—limited relief Menthol 10% —(BENGAY®)—No relief Patient began applying Cryogel to muscle of injury or tear, and began experiencing relief within a few hours. One month later. Patient reports resolution of pain, and soreness after initiating Cryogel. Patient continues to use Cryogel as needed.

Case #18: Cryogel CBD 500 mg is a topical hemp applicator designed to assist in relieving joint, muscle, and arthritic aches and pains. 63 y/o female presenting burning, stinging pain, and inflammation in upper right elbow. Patient reported trying the following to relieve soreness and pain: Ibuprofen 200 mg—Take 2 tablets TID—limited relief. BIOFREEZE®—Roll on Gel—Applied 4-5 times to affected area daily—minor relief. Menthol 10% —(BENGAY®)—No relief. Patient began applying Cryogel to muscle of injury or tear, and began experiencing relief within a few hours. One month later. Patient reports resolution of pain, and soreness after initiating Cryogel. Patient continues to use Cryogel as needed.

Case #19: Cryogel CBD 500 mg is a topical hemp applicator designed to assist in relieving joint, muscle, and arthritic aches and pains. 39 y/o male presenting bilateral inflammation of the knees post exercise/running. Patient reported trying the following to relieve soreness and pain: Ibuprofen 200 mg—Take 2 tablets TID—limited relief Tylenol 500 mg—Take 2 tablets BID—Limited relief Celebrex 200 mg—Take 1 capsule by mouth daily—Limited Relief. BIOFREEZE®—Roll on Gel—Applied 4-5 times to affected area daily—minor relief. Menthol 10% —(BENGAY)—No relief. Patient began applying Cryogel to muscle of injury or tear, and began experiencing relief within a few hours. 4 days later. Patient reports resolution of pain, and soreness after initiating Cryogel. Patient continues to use Cryogel as needed.

Case #20: Cryogel CBD 500 mg is a topical hemp applicator designed to assist in relieving joint, muscle, and arthritic aches and pains. 34 y/o male presenting inflammation of the right wrist due to possible sprain. Patient reported trying the following to relieve soreness and pain: BIOFREEZE®—Roll on Gel—Applied 4-5 times to affected area daily—minor relief. CBDMD 750 mg CBD—Roll on Applicator—Applied 4-5 times daily—minor relief. Patient began applying Cryogel to muscle of injury or tear, and began experiencing relief within a few hours. 3 days later. Patient reports resolution of pain, and soreness after initiating Cryogel. Patient continues to use Cryogel as needed.

Case #21: Cryogel CBD 500 mg is a topical hemp applicator designed to assist in relieving joint, muscle, and arthritic aches and pains. 65 y/o male presenting inflammation of the right knee. Patient reported trying the following to relieve soreness and pain: Applied ice, and alternating with heat to reduce swelling and pain. Ibuprofen 200 mg—Take 2 tablets BID—Limited Relief Tylenol 500 mg—Take 2 tablets BID—No relief Patient began applying Cryogel to muscle of injury or tear, and began experiencing relief within a few hours. 4 days later. Patient reports resolution of pain, and soreness after initiating Cryogel. Patient continues to use Cryogel as needed.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A composition comprising:
   3.5-8.5 mg/ml hemp cannabidiol (cannabinoid);
   2.0-4.0 weight percent (wt %) menthol;
   an herb extract of *Arnica montana*, wherein an amount of the *Arnica montana* herb extract is 1.0-5.0 wt %;
   1.0 to 3.0 wt % herb extract of *Boswellia serrata*; and
   qs with water, wherein the amount of hemp cannabidiol and menthol is synergistic for treating inflammation and pain, and wherein the composition is free of any tetrahydrocannabinol.

2. The composition of claim 1, further comprising at least one of isopropyl alcohol, or propylene glycol.

3. The composition of claim 1, further comprising at least delivery vehicle or gel selected from: glycerin, Carbomer (polyacrylic acid), Hydrated Silica, Isopropyl Alcohol, Propylene Glycol, Glycerin, Carbomer 940, Aminomethyl Propanol, or Methyl Paraben.

4. The composition of claim 1, further comprising one or more additional herb extracts selected from *Uricaria Tomentosa* Extract, or *ILEX Paraguariensis* Leaf Extract.

5. The composition of claim 1, wherein the composition is defined further as comprising hemp cannabidiol (cannabinoid) 3.5-8.0 mg/ml weight percent (wt/%);
   menthol 2.0-3.0 wt % weight percent; *Arnica montana* 1.0-5.0 wt % weight percent;

camphor 0.1-5.0 wt %; *Boswellia serrata* extract 1.0 to 3.0 wt % weight percent; isopropyl alcohol <30 wt %; glycerin <6.0 wt %; camphor terpene 0.1-5.0 wt %; and qs with water.

6. The composition of claim 1, wherein the composition is free of any tetrahydrocannabinol.

7. A composition consisting essentially of:

hemp cannabidiol, wherein an amount of hemp cannabidiol is 3.5-8.5 mg/ml;

menthol 2.0-4.0 weight percent (wt %);

*Arnica montana* 0.1-5.0 wt %;

camphor 0.1-5.0 wt %;

*Boswellia serrata* extract 1.0 to 3.0 wt %;

camphor terpene 0.1-5.0 wt %;

isopropyl alcohol <30 wt %;

glycerin <6.0 wt %; and qs with water, wherein the amount of hemp cannabidiol and menthol composition is synergistic for treating inflammation and pain, and wherein the composition is substantially free of any tetrahydrocannabinol.

* * * * *